United States Patent [19]

Norman, Jr.

[11] Patent Number: 5,919,444

[45] Date of Patent: *Jul. 6, 1999

[54] METHOD FOR DECREASING SEVERITY OF ACUTE AND CHRONIC PANCREATITIS

[75] Inventor: James G. Norman, Jr., Tampa, Fla.

[73] Assignee: University of South Florida, Tampa, Fla.

[*] Notice: This patent is subject to a terminal disclaimer.

[21] Appl. No.: 08/603,784

[22] Filed: Feb. 20, 1996

Related U.S. Application Data

[63] Continuation-in-part of application No. 08/167,698, Dec. 15, 1993, Pat. No. 5,508,262.

[51] Int. Cl.⁶ .............................. A61K 45/05; C07K 5/00
[52] U.S. Cl. .......................... 424/85.2; 424/85.1; 514/8; 514/12; 514/21; 530/351
[58] Field of Search .................................. 514/8, 12, 21; 424/85.1, 85.2; 530/351

[56] References Cited

U.S. PATENT DOCUMENTS

| | | | |
|---|---|---|---|
| 4,959,217 | 9/1990 | Sanders et al. | 424/473 |
| 5,167,616 | 12/1992 | Haak et al. | 604/20 |
| 5,169,383 | 12/1992 | Gyory et al. | 604/20 |
| 5,225,182 | 7/1993 | Sharma | 424/9 |
| 5,508,262 | 4/1996 | Norman, Jr. | 514/8 |

FOREIGN PATENT DOCUMENTS

WO921272  8/1992  WIPO.

OTHER PUBLICATIONS

Aiura et al., "Interleukin–1 receptor antagonist prevents *Staphylococcus epidermidis*–induced hypotension . . . " *Infection and Immunity*, pp. 3342–3350 (1993).

Bamba et al., "Serum levels of interleukin–1 beta and interleukin–6 in patients with chronic pancreatitis" *J. Gastroenterology*, 29(3):314–19, (1994).

Cioffi et al., "Leukocyte responses to injury" *Arch Surg*, 128:1260–1267 (1993).

Coticchia et al., "Peritoneal fluid in human acute pancreatitis blocks hepatic mitochondrial respiration" *Surgery*, 100(5):850–855 (1986).

Dinarello et al., "Anticytokine strategies in treatment of systemic inflammatory response syndrome" *JAMA*, 269:1829–1834 (1993).

Dolan et al., "Biphasic tumor necrosis factor release in experimental acute pancreatitis" *Gut*, 35:A575, 1994 (Abstract).

Driscoll, "The Preclinical New Drug Research Program of the National Cancer Institute (1984)" *Cancer Treatment Reports*, 68:63–76.

Fischer et al., "A comparison between the effects of interleukin–1 administration and sublethal endotoxemia in primates" *Am J. Physiol*, 261:R442, (1991).

Formela et al., "Demonstration of tumor necrosis factor in pancreatic acinar cells by in situ hybridisation in a model . . . " *Gut*, 35:A575, 1994 (Abstract).

Granowitz et al., "Effect of interleukin–1 (IL–1)blockade on cytokine synthesis: I. IL–1 receptor antagonist . . . " *Blood*, 79:2356–2363, (1992b).

Grewal et al., "Anti–TNF therapy improves survival and ameliorates the pathophysiologic sequelae in acute pancreatitis . . . " *Am. J. Surg.*, 171:274–280 (1996) plus abstract.

Gross et al., "Inflammatory mediators and cytokines–new aspects of pathophysiology and assessment of severity of acute pancreatitits?" *Hepato–Gastroenterol*, 40:522–529, (1993).

Guice, et al., "Neutrophil–dependent, oxygen–radical mediated lung associated with acute pancreatitis" *Ann Surg*, 210: 740–747 (1989).

Imrie and Whyte, "A prospective study of acute pancreatitis" *Br J Surg*, 62:490–494 (1975).

Jacobs et al., "Acute pancreatitis: analysis of factors influencing survival" *Ann Surg*, 185:43–51, (1977).

Kelly et al, "Microvasculature of the pancreas, liver, and kidney in caerulein induced pancreatitis" *Arch Surg*, 128:292–295 (1993).

Kuida et al., "Altered cytokine export and apoptosis in mice deficient in interleukin–1β converting enzyme" *Science*, (1995).

Kusske et al., "Interleukin 10 (IL–10) prevents death in lethal necrotizing pancreatitis (AP) in mice" *Society of University Surgeons* 57th Annual Meeting, Feb., 1996, p. 40 (abstract).

Lowry, "Cytokine mediators of immunity and inflammation" *Arch Surg*, 128:1235–1241, (1993).

McKay et al., "Systemic complications in acute pancreatitis are associated with increased monocyte cytokine release" *Gut*, 35:A575, (1994) (Abstract).

Mohler, "The use of soluble TNF receptors as inhibitors of inflammation" *Proceedings of Regulation of Cytokine Activity for Therapeutic Development*, Mar. 3, 1994 Washington, D.C. [n/a].

Norman et al., Rapid elevation of systemic cytokines during acute pancreatitis and their origination within the pancreas *Surg Forum* XLV:191–194 (1994a).

Norman and Franz, "Acute phase cytokines during experimental acute pancreatitis" *Cytokine*, (1994b). [never published].

Norman et al., "Decreased severity of experimental acute pancreatitis by pre or post treatment . . . " *28th Annual Meeting, Pancreas Club, Inc.* (New Orleans, LA) May (1994d). (Abstract 1994, p. 23 and reference).

(List continued on next page.)

Primary Examiner—Cecilia J. Tsang
Assistant Examiner—Bennett Celsa
Attorney, Agent, or Firm—Kohn & Associates

[57] ABSTRACT

A method for treating acute or chronic pancreatitis comprising administering an effective amount of an Interleukin-1 (IL-1) block to antagonize IL-1 production, and in one embodiment by inhibiting IL-1 production at the source, or a pharmaceutically acceptable salt thereof to a person who has pancreatitis. One such IL-1 block is an Interleukin-1 converting enzyme (ICE) antagonist.

6 Claims, 3 Drawing Sheets

OTHER PUBLICATIONS

Norman et al., "Interleukin–1 receptor antagonist decreases severity of acute pancreatitis" *Surgery,* 117:648–655 (1995a).

Norman et al., "Decreased mortality of severe acute pancreatitis after proximal cytokine blockade" *Annals of Surgery,* 221:625–634 (1995b).

Okusawa et al., "Interleukin–1 induces a shock–like state in rabbits" Synergism with tumor necrosis factor . . . *J Clin Invest,* 81:1162 (1988).

Oppenheim et al., "Clinical applications of cytokines; role in pathogenesis diagnosis and therapy" Oxford University Press, NY, NY (1993) (related pages only).

Pappas et al., "Pancreatitis–associated ascitic fluid: effect on oxygen consumption of liver cells" *Soc Exp Biol Med.,* 169:438–444 (1982).

Physicians' Desk Reference®: pp. 1654–1658 (1994).

Ranson and Spencer, "Role of peritoneal lavage in severe acute pancreatitis" *Ann Surg,* 187:565–573, (1978).

Rodgers and Carey, "Peritoneal lavage in experimental pancreatitis in dogs" *Amer J. Surg,* 111:792–794 (1966).

Saluja et al., "In vivo rat pancreatic acinar cell function during supramaximal stimulation with caerulien" *Amer Physiological Society,* G702–710 (1985).

Spillenaar Bilgen et al., "Attempts to reduce post–transplant pancreatitis in rats and dogs with the somatostatin analogue . . . " *Transplant Proceed,* 21:2829–2830 (1989).

Steer, "How and where does acute pancreatitis?" *Arch Surg,* 127:1350–1353 (1992).

Steinberg and Tenner, "Acute pancreatitis" *N Eng J Med,* 330:1198–1220 (1994).

Stone and Fabian, "Peritoneal dialysis in treatment of acute alcoholic pancreatitis" *Surg Gynecol Obstet,* 150:878–882 (1980).

Van Ooijen et al., "Significance of thromboxane $A_2$ and prostaglandin in acute necrotizing pancreatitis in rats" *Digestive Disease and Sciences,* 35:1078–1084 (1990).

Waage and Espevik, "Interleukin–1 potentiates the lethal effect of tumor necrosis factor/cachectic in mice" *J Exp Med,* 167:1987 (1988).

Wakabayashi et al., "A specific receptor antagonist for interleukin–1 prevents *E. coli* induced shock in rabbits" *FASEB,* 5:338 (1991).

Zhu et al., "A somatostatin analogue is protective against retrograde bile salt–induced pancreatitis in the rat" *Pancreas,* 6:609–613 (1991).

Elford et al., J. Pharm. (Jun. 1995) vol. 115 pp. 601–606.

Miller et al, J. Immun vol. 154, No. 3 (Feb. 1, 1995) pp. 1331–1338.

Goodman & Gilman's "The Pharmacological Basis of Therapeutics" 6th Ed. (MacMillan Pub. 1980) pp. 1738–1740.

METHOD FOR DECREASING SEVERITY OF ACUTE AND CHRONIC PANCREATITIS

This is a continuation-in-part of application Ser. No. 08/167,698 filed on Dec. 15, 1993 now U.S. Pat. No. 5,508,262.

BACKGROUND OF THE INVENTION

1. Technical Field

The present invention relates to a method for treating acute and chronic pancreatitis.

2. Background Art

Acute pancreatitis is a common clinical problem which remains evasive of specific therapy (Leach et al., 1992). Each year more than 210,000 admissions to U.S. hospitals are caused by acute pancreatitis while another 150,000 are due to chronic pancreatitis. Pancreatitis is most often caused by alcoholism or biliary tract disease. Less commonly, it is associated with hyperlipemia, hyperparathyroidism, abdominal trauma, vasculitis or uremia. The average length of hospitalization for the acute disease is 12.4 days, with a significant number of patients staying much longer because of associated complications.

Chronic ethanol abuse is the most common cause of acute and chronic pancreatitis in the West, yet the pathophysiology of this disease remains poorly understood (Steinberg and Tenner, 1994). There are few medical therapies or pharmacologic agents currently available which have been shown to decrease the severity, duration, complication rate, or mortality for this common disease. Care for these patients, regardless of the etiology, remains primarily supportive, with attention directed towards maintaining an adequate circulating blood volume, supporting renal and respiratory systems, and providing adequate nutrition. This lack of specific therapy has prompted a great number of prospective trials during the past two decades in hopes of finding some way to decrease the progression and severity of this disease. To date, specific therapy remains unknown and a search for new, more effective modalities is necessary.

The overall mortality for acute pancreatitis varies between 6 and 18% and can raise as high as 50% in the more fulminant form (Steinberg and Tenner, 1994; Imrie and Whyte, 1975; Jacobs et al., 1977). Interestingly, the prognosis for this disease appears more dependent upon its systemic manifestations and complications than upon the severity of the local pancreatic inflammation (Imrie and Whyte, 1975; Jacobs et al., 1977). In fact, as many as 60% of deaths from acute pancreatitis which occur within one week of onset can be attributed to adult respiratory distress syndrome (ARDS), which cannot be distinguished from sepsis-associated ARDS (Steinberg and Tenner, 1994; Jacobs et al., 1977).

Chronic pancreatitis develops in those patients who continue to drink after their first bout of pancreatitis or those with gallstone pancreatitis for unknown reasons. The recurrent bouts of acute pancreatitis subsequently become less severe and less life threatening. The typical patient with chronic pancreatitis, however, is admitted to the hospital approximately one to two times per year for the rest of their lives. These patients have a decreased life span when compared to their peers (Imrie and Whyte, 1975; Steinberg and Tenner, 1994). Despite the less severe course of the disease, it causes chronic debilitating pain and numerous hospitalizations and loss of productivity. These patients often have chronic pain to such a degree that they become dependent upon narcotics or require operative intervention in attempts to remove or oblate some of the chronically inflamed pancreas.

It was noted in 1966 that dogs suffering from an experimental model of severe pancreatitis did not die as frequently if their abdomen was washed with Ringer's lactate to remove the pancreatic associated ascitic fluid (PAAF) (Rodgers and Carey, 1966). It was suggested that peritoneal lavage removed some toxic substance(s) within the PAAF.

During the 1970s and early 1980s, several investigators examined the toxic effect of PAAF on multiple organ systems. Ellison and colleagues conducted a number of experiments in an attempt to determine the factor or factors present in the pancreatic ascites which was responsible for the systemic effects seen during acute pancreatitis. Their studies showed that a substance was present in PAAF which was responsible for the hemoconcentrating effect, as well as hypotension seen during severe attacks (Ellison et al., 1981). They subsequently demonstrated that ARDS could be induced when the lungs of healthy animals were lavaged with small amounts of PAAF. Hepatic mitochondrial respiration and oxygen consumption was diminished in vitro when hepatic cells were exposed to PAAF (Coticchia et al., 1986; Pappas et al., 1978). This toxin, therefore, was not specific for one cell or tissue type; in fact, it has profound effects on all organ systems examined.

This "cytotoxic factor" had not been positively identified, yet several clinical studies by Ranson et al. (1978), and Stone et al. (1980) supported the presence of this group of toxin(s) in humans by showing that peritoneal lavage early in the course of acute pancreatitis could decrease the incidence and severity of systemic sequelae and decrease overall mortality. Recent studies by the applicant has documented the presence of inflammatory cytokines within pancreatic ascites (human and animal) supporting the role of these mediators in the development of systemic complications associated with acute pancreatitis. (Norman et al, 1994a, Norman et al, 1995a,b; co-pending U.S. patent application Ser. Nos. 08/167,698 and 08/369,386).

Over the past decade, a somatostatin analog has undergone several clinical, as well as laboratory trials, in an attempt to show beneficial effects of suppressing pancreatic exocrine function pharmacologically during acute pancreatitis. The majority of investigators have shown beneficial effects only with treatment prior to the onset of pancreatitis, and disappointing results when somatostatin was given after the acute inflammatory process had started (Murayama et al., 1990; Zhu et al., 1991; Spillenaar et al., 1989).

A curious aspect of acute pancreatitis is the systemic response which is seen following inflammation initiated within the pancreas. Acute pulmonary, renal, and hepatic failure, generalized water retention, hypocalcemia, hypoxia, and acid/base disturbances are all common complications of pancreatitis. The mechanism for the involvement of these other organ systems probably involves activation of the cytokine cascade, including interleukin-1 (IL-1), interleukin-6 (IL-6), and tumor necrosis factor (TNF) in a manner not significantly different from sepsis syndromes (Heath et al., 1993; Larson and Henson, 1983; Deitch, 1992; Michie and Wilmore, 1990; Dinarello et al., 1993). Serum levels of these peptides have been shown to correlate to a high degree with the severity of acute pancreatitis in humans, and can also be demonstrated within pancreatic ascites (Heath et al., 1993; Ellison et al., 1981). Other findings have shown that much of the intrinsic pancreatic damage seen in acute pancreatitis is due to the release of cytokines from macrophages and other white blood cells which migrate into the damaged gland (Steer, 1992; Tani et al., 1987; Van Ooijen et al., 1990; Schoenberg et al., 1992; Kelly et al., 1993; Gross et al., 1993; Guice et al., 1991; Heath et al., 1993; Norman and Franz, 1994b; Norman et al., 1994a; Norman et al., 1995a; Norman et al., 1994c; Norman et al., 1994d; Leach et al., 1992; Dinarello et al., 1993; Grewal et al., 1994a; Grewal et al., 1994b; Cioffi et al., 1993; Lowry, 1993; McKay et al., 1994; Formela et al., 1994; Dolan et al., 1994; Oppenheim et al., 1993).

Recent evidence investigating the pathophysiology of chronic pancreatitis has shown that IL-1 may play an important role in this form of pancreatitis as well (Bamba et al, 1994). These authors followed thirty-three patients with chronic pancreatitis and have found each one to have sustained elevations in serum Interleukin-1. Applicants have found, using immunohistochemistry with similar patients, that IL-1 is indeed present in the chronically inflamed human pancreas whereas it is never found in the normal pancreas. Bamba and his colleagues have subsequently investigated the role of IL-1 in another fifty patients with chronic pancreatitis (Bamba et al, J. Gastroenterology 1996, in press) and has suggested that IL-1 plays a very important role in the maintenance of chronic inflammation within the gland. This chronic inflammation is believed to be the cause of their pain and hospitalization.

Guice et al. (1989) have shown that pancreatitis-associated adult respiratory distress syndrome (ARDS) is to a large degree neutrophil mediated and is not iron-dependent or hydroxyl-radical mediated. They suggested that the process of acute pancreatitis leads to neutrophil recruitment, sequestration, and adherence to alveolar capillary endothelial cells with lung injury ultimately a result of neutrophil-generated products including cytokines. These cytokines are active in low concentrations (picomolar-femtomolar) and are not produced in the normal disease-free state. They may function as mediators in a autocrine, paracrine, and endocrine fashion, and, therefore, may induce inflammation or tissue damage locally, as well as at great distances (Dinarello et al., 1993; Cioffi et al., 1993; Lowry, 1993; Oppenheim et al., 1993).

The administration of IL-1 to rabbits (Wakabayashi et al., 1991; Okusawa et al, 1988; Ohlsson et al., 1990; Aiura et al., 1991) and primates (Fischer et al., 1991) has been shown to result in hypotension, tachycardia, lung edema, renal failure, and, eventually, death, depending on the dose. These signs and symptoms are similar to those demonstrated by patients with severe acute pancreatitis. When the serum from the IL-1 treated animals is examined, the elevation of other cytokines is evident, mimicking the levels seen in acute pancreatitis in humans (Guice et al., 1991; Heath et al., 1993).

Recent investigations have shown that serum levels of inflammatory cytokines correlate to a high degree with the clinical severity of pancreatitis. In a recent publication, Heath et al. (1993) showed significantly higher serum IL-6 levels (approximately 10-fold higher) in patients with severe acute pancreatitis than those with mild acute pancreatitis (Heath et al., 1993). These researchers demonstrated that the clinical course of those patients with higher levels of IL-6 was more complicated and protracted than those with low or undetectable IL-6. A similar study presented at the 1994 meeting of the Pancreatic Society of Great Britain and Ireland showed elevation IL-1, IL-6, and Tumor necrosis factor-α (TNF-α) in all patients with severe pancreatitis which correlated very well with systemic symptoms, complications, and mortality (McKay et al., 1994).

IL-1, IL-6, and TNF-α can be isolated from pancreatic ascites in both humans and experimental animals (Heath, 1993; Norman and Franz, 1994b; McKay et al., 1994; Dolan et al., 1994), and again, levels correlate with the severity of disease. It is interesting to note that the molecular weight of these three cytokines is between 10,000 and 25,000 daltons as suggested by Carey and associates as early as 1983.

Applicant has also shown that TNF-α, IL-1 and IL-6 are rapidly and predictably elevated during acute pancreatitis and that levels are highest within the pancreas itself (Norman et al., 1994a). Applicant suggest that this is evidence of cytokine production within the pancreas which may be partially cleared by the liver.

There seems little doubt now that several inflammatory cytokines are activated and detectable in pathologic concentrations in the serum and ascites of humans, as well as experimental animals, during bouts of acute and chronic pancreatitis.

This complements the large body of evidence currently available which supports the roles of IL-1 and TNF as major mediators of the systemic response to diseases such as sepsis and pancreatitis and as activators of the remaining members of the cytokine cascade (Dinarello et al., 1993). Fischer et al. (1991) demonstrated that the administration of a naturally occurring antagonist to IL-1 will significantly blunt the cytokine cascade and improve survival in baboons given a lethal dose of live bacteria. In this study, IL-1 receptor antagonist (IL-1ra) significantly attenuated the decrease in mean arterial pressure and cardiac output and improved survival over control. The systemic IL-1 and IL-6 responses observed as a result of the bacteremia were diminished significantly, correlating with a decrease in the systemic response to the sepsis.

Studies by Aiura et al. (1991) have shown that IL-1ra is protective in a rabbit model of hypotensive gram-positive septic shock. The administration of IL-1ra in this animal model has been shown to maintain mean arterial pressure compared to control, as well as decreasing lung water and maintaining urine output. This work demonstrated the role of IL-1 and the protective role of IL-1ra in gram-positive shock which was thought to be due to a separate mechanism from gram-negative shock. The common pathway for the systemic manifestations of these two different models of shock has been shown to involve IL-1 as a central mediator. Evidence is mounting for the role of IL-1 as a principal mediator in a patient's clinical response to multiple different stresses regardless of the etiology (including pancreatitis).

Grewal et al. (1994) have shown that treatment with anti-TNF antibody therapy improves survival in an animal model of acute pancreatitis when given prophylactically. Treatment of humans with antibodies (monoclonal or polyclonal) carries significant risks. The antibodies represent a foreign protein which is itself antigenic to the recipient. This has been shown to be a problem in approximately 3–5% of all patients receiving an initial treatment with antibodies (PDR, 1994). However, the incidence of complications, including death from serum sickness, has been shown to increase to as much as 30% with repeat administration. For these reason no current manufacture of antiserum or antibodies allows the repeat administration of these proteins.

An additional theoretical problem with antibody therapy when applied to antagonism of human cytokines is that the affinity of the cytokine for its membrane bound receptor is several orders of magnitude (3 to 5) higher than is the affinity of the proposed blocking antibody for the cytokine in question. The stoichiometry dictates that the cytokine has an increased chance of binding to the receptor than to the corresponding antibody, thereby mediating its detrimental effects. Since cytokines are known to illicit their intracellular responses and subsequent detrimental effects when only a single cytokine has found its way to a membrane bound receptor, the importance of complete blockade of the circulating cytokine becomes of paramount importance. (Oppenheim, et al., 1993).

Hence, to be effective on repeated administration, an antibody should not be antigenic. In general, efforts to reduce antigenicity have included forming chimeric molecules that comprise human antibody constant domains fused with murine antibody variable domains humanizing murine antibodies so that all but the six hypervariable loops of the antibody combining site are of human sequence and, most definitively, producing human antibodies in vitro and thus bypassing the need for immunization in other species. However, these procedures are not always available, do not always provide antibody with the necessary avidity and are costly to provide. Therefore, other treatment modalities must be explored.

P U.S. Pat. Nos. 4,522,827 and 4,902,708 disclose methods of treating acute pancreatitis. However, none of these patents take into effect the specific pathology of the disease, thereby proposing treatments which are not specific and are directed to the symptoms only, not the underlying mechanism.

U.S. Pat. No. 5,196,402 discloses the use of S-adenosyl methionine for the use of treatment of pancreatitis in the context of a complication in the graft rejection in pancreas transplant, a very uncommon procedure. The patent does not address acute pancreatitis as a disease in the nontransplant patient. The vast majority of cases of pancreatitis are not associated with pancreatic transplants.

From the above review, it is apparent that systemic complications associated with severe pancreatitis are mediated by pro-inflammatory cytokines. Applicant has previously shown that proximal blockade of the cytokine cascade at the level of the interleukin-1 (IL-1) receptor results in attenuated production of these inflammatory mediators and is associated with a significant decrease in the severity of pancreatitis as set forth in co-pending U.S. patent application Ser. No. 167,698 assigned to the assignees of the present invention and incorporated herein by reference. These changes are associated with a survival advantage, therefore it would be useful to increase the efficacy of proximal cytokine antagonism in order to decrease the mortality of acute and chronic pancreatitis.

Additional treatments are needed which take into account that the local, as well as systemic, effects seen during pancreatitis are due to activation of the cytokine cascade whereby proximal inhibition of this cascade will decrease the severity of the inflammatory process.

SUMMARY OF THE INVENTION

According to the present invention, a method for treating acute or chronic pancreatitis is presented. The method comprises administering an effective amount of an Interleukin-1 (IL-1) block to antagonize IL-1 production to a patient with pancreatitis. In one embodiment the block is provided by an Interleukin-1 converting enzyme (ICE) antagonist or a pharmaceutically acceptable salt thereof to a person with pancreatitis.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

The present invention is a method for treating acute or chronic pancreatitis. The method comprises administering an effective amount of an Interleukin-1 (IL-1) block to a patient with pancreatitis. By IL-1 block is meant an antagonist that will antagonize IL-1 production by inhibiting IL-1 production. In one embodiment the block is provided by an Interleukin-1 converting enzyme (ICE) antagonist or a pharmaceutically acceptable salt thereof to a person with pancreatitis. In a further embodiment IL-10 is used as an IL-1 block.

The term antagonist or antagonizing (and block) is used in its broadest sense. The terms can include any mechanism or treatment which results in inhibition, inactivation, blocking or reduction in IL-1 production. The block can occur during translation and transcription, during the post-transcriptional period or by preventing secretion. Interleukin-1 converting enzyme (ICE) antagonist is an example of a block of post-transcriptional processing. IL-10 is an example of inhibition at the mRNA level (Kusske et al, 1996).

Pancreatitis is a disease of complex etiology resulting in activation of several of the pro-inflammatory cytokines including interleukin-1 (IL-1). IL-1 is a powerful cytokine which has been shown to play an integral role in the production of pancreatitis-induced acinar necrosis and the subsequent development of distant organ dysfunction. The use of antagonists to the IL-1 receptor has been shown to attenuate the severity of pancreatitis by decreasing pancreatic enzyme release, lessening necrosis, and improving survival.

In a previous study as set forth in Example 1 herein below applicants utilized IL-1ra which is a naturally occurring peptide secreted by macrophages in response to many of the same stimuli which cause the secretion of IL-1 itself. IL-1ra is the only known naturally occurring cytokine antagonist and recognizes receptors on various cell types and blocks IL-1 mediated responses by occupying the receptor. The present invention improves on these findings by antagonizing IL-1 production directly.

IL-1 is produced by neutrophils and macrophages through the conversion of the pro-hormone "pre-IL-1" to its active form by a specific intracellular enzyme called interleukin-1 converting enzyme (ICE). It has been shown that blocking this enzyme results in an inability for leukocytes to produce IL-1 (Kuida et al., 1995). Since the production of IL-1 is dependent upon the activity of this enzyme, applicant investigated the use of an antagonist to this enzyme hypothesizing that this agent could attenuate the severity of pancreatitis in a similar fashion to IL-1 receptor blockade. As shown in Example 2, the use of an ICE antagonist, VE-13045, a peptidyl ICE inhibitor, having the formula carbobenzyloxy-Val-Ala-Asp(O-et)-CH$_2$O-dichlorobenzoate and structural formula did attenuate the severity of pancreatitis.

A second series of experiments, as set forth in Example 3, utilized transgenic mice which were bred to be genetically deficient of the ICE gene. These animals do not produce the ICE enzyme and cannot make active IL-1. If these animals show a decrease in the severity of pancreatitis, then it would provide further proof that ICE antagonism is beneficial in this disease. As shown in the Example herein below there was a decrease in the severity of pancreatitis in these animals.

The IL-1 block is administered and dosed in accordance with good medical practice, taking into account the nature of the compound as to the route of administration wherein biological activity is maintained, clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to obtain blood levels which have been shown to be high enough to achieve near complete blockade (antagonism) of circulating IL-1. Improved survival rate, more rapid recovery including decreased time in ICU and more rapid return to regular diet, or improvement or elimination of symptoms are also measurements of effective amount.

In the method of the present invention, the IL-1 block can be administered in various ways, taking into account the nature of the compound as to the route of administration wherein biological activity is maintained. For example, the ICE blocker VE-13045, a peptidyl ICE inhibitor, can be administered orally. Alternatively, IL-10 can be administered intravenously (Kusske, et al, 1996).

It should be noted that the IL-1 block can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man.

It is noted that humans are treated generally longer than the mice exemplified herein which treatment has a length proportional to the length of the disease process and drug effectiveness. The doses may be single doses or multiple doses over a period of several days. The treatment generally has a length proportional to the length of the disease process and drug effectiveness and the patient species being treated.

When administering the IL-1 block parenterally, the IL-1 block will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions.

The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds and with maintaining biological activity.

Sterile injectable solutions can be prepared by incorporating the compounds utilized in practicing the present invention in the required amount of the appropriate solvent with various of the other ingredients, as desired.

A pharmacological formulation of the IL-1 block can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. No. 5,225,182; U.S. Pat. No. 5,169,383; U.S. Pat. No. 5,167,616; U.S. Pat. No. 4,959,217; U.S. Pat. No. 4,487,603; U.S. Pat. No. 4,486,194; U.S. Pat. No. 4,447,233; U.S. Pat. No. 4,447,224; U.S. Pat. No. 4,439,196; and U.S. Pat. No. 4,475,196. Many other such implants, delivery systems, and modules are well known to those skilled in the art.

A pharmacological formulation of the IL-1 block utilized in the present invention can be administered orally to the patient. Conventional methods such as administering the compounds in tablets, suspensions, solutions, emulsions, capsules, powders, syrups and the like are usable. Known techniques which deliver the IL-1 block orally or intravenously and retain the biological activity are preferred.

In one embodiment for acute pancreatitis, the IL-1 block can be administered initially by intravenous injection to bring blood levels of the IL-1 block to a suitable level. The patient's IL-1 block levels are then maintained by an oral dosage form, although other forms of administration, dependent upon the patient's condition and as indicated above, can be used. The quantity of IL-1 block to be administered will vary for the patient being treated and will vary from about 100 ng/kg of body weight to 100 mg/kg of body weight per day and preferably will be from 10 $\mu$g/kg to 10 mg/kg per day.

In a second embodiment the IL-1 block is an ICE antagonist VE-13045, a peptidyl ICE inhibitor, which is administered orally, at an effective high dose during acute pancreatitis and lower effective doses to chronic pancreatitis patients to decrease "flare-ups" of the disease.

The IL-1 block can be administered in combination with other drugs or singly consistent with good medical practice. The other drugs can be somatostatin or an analog (i.e., Sandostatin®) and prostaglandin inhibitors (i.e., non-steroidal, anti-inflammatory drugs such as aspirin, indomethacin, ibuprofen, etc.). Additionally, steroids or other drugs designed to suppress the immune system and other synthetic or recombinant antagonists or blockers to cytokines (e.g., soluble IL-1 receptors, soluble IL-6 receptors or others; monoclonal antibodies to IL-1, IL-6, TNF or others, etc.) can be administered. Further, nitric oxide inhibitors or antagonists, platlet activating factor antagonists, free radical scavengers or antioxidants, antagonists or blockers of complement, ecosinoids or their antagonists, anti-proteases and antibiotics, as appropriate, can also be administered.

In one embodiment the IL-1 block is administered in combination with IL-1ra and/or tumor necrosis factor soluble receptor (TNFsr) as cytokine cascade blockers.

The IL-1 block or combination of IL-1 block and other drugs is administered and dosed taking into account the clinical condition of the individual patient, the site and method of administration, scheduling of administration, and other factors known to medical practitioners. The "effective amount" for purposes herein is thus determined by such considerations as are known in the art as described herein above.

The safety of IL-1ra after intravenous administration has been demonstrated during the past four years in mice, rats, rabbits, dogs, primates, and humans (Wakabayashi et al., 1991; Ohlsson et al., 1990; Aiura et al, 1991; Fischer et al, 1991; Waage and Espevik, 1988; Fischer et al, 1992; Granowitz et al., 1992, 1992b). In normal volunteers, IL-1ra has been demonstrated to have a half-life of approximately twenty-seven minutes after intravenous administration and the plasma clearance of IL-1ra appeared to correlate with creatine clearance (Bloedos et al., 1992). In general, a continuous IV drip is used to maintain adequate circulating levels with 2.0 mg/kg/hr being the preferred embodiment. Hence, there already exists a regimen for IL-1ra administration for humans.

In a preferred embodiment, recombinant soluble TNF (rTNFsr) is used as the cytokine antagonist. rTNFsr has been used in both Phase I and Phase II clinical trials. (Mohler, 1994) Therefore, the regimen for rTNFsr has been established for humans. Pharmokinetic studies to date indicate that 2 mg/kg body weight administered to a patient every 24 hours should obtain blood levels which are high enough to achieve near complete blockade of circulating tumor necrosis factor. The half-life of the dimeric form of rTNFsr is at or just above 26 hours in humans. This allows the use of a once-a-day dosage regimen in a preferred embodiment when appropriate.

The above discussion provides a factual basis for treating a patient with pancreatitis with an Interleukin-1 (IL-1) block to antagonize IL-1 production by inhibiting IL-1 production at the source. The methods used with and the utility of the present invention can be shown by the following non-limiting examples and accompanying figures.

EXAMPLE 1

Acute edematous, necrotizing pancreatitis was induced in adult male Swiss mice weighing more than 35 grams using caerulein—an analog of cholecystokinin. Mice were divided into four groups with three of the groups receiving caerulein 50 $\mu$g/kg by intraperitoneal (IP) injection in four doses over three hours as previously described. (Murayama, et al., 1990; Tani, et al., 1987; Schoenberg et al., 1992; Heath et al., 1993; Saluja et al., 1985; Manso et al., 1992).

Group 1 was a control group (n-9) which received only IP saline injections. Group 2 (n=12) was an untreated disease control. Group 3 (n=12) received three injections (10 mg/kg/hr) starting one hour prior to induction of pancreatitis. Group 4 (n=12) received three injections (10 mg/kg/hr) starting one hour after induction of pancreatitis.

The IL-1ra used in this study is produced in *E. coli* by Synergen Corporation (Boulder, Colo.) by utilizing recombinant DNA technology and is identical to the non-glycosylated human form of human IL-1ra except for the addition of one terminal methionine amino acid.

After nine hours, all animals were euthanized, the blood collected, and the pancreata surgically excised and weighed. Serum was assayed for amylase, lipase, IL-6, and TNF levels. Each pancreas was fixed, stained, and graded histologically in a blinded fashion for interstitial edema, granulocyte infiltration, acinar vacuolization, and acinar cell necrosis as described previously.(Tani et al., 1987; Driscoll, 1984; Saluja et al., 1985) Additionally, serum levels of IL-1ra were determined, therefore allowing comparisons between dosage, serum level, systemic cytokine response, and degree of pancreatic damage.

IL-6, Il-1, IL-1ra,and TNF were measured by commercially available ELISA kits (Genzyme Corp., Boston, Mass.). All specimens were run in triplicate. Serum levels of amylase and lipase were measured on a Kodak Ectachem 700 automated analyzer (Eastman Kodak Company, Rochester, N.Y.).

Histologic slides were prepared as is known in the art after rapid excision and subsequent fixation in 10% formalin. The tissues were paraffin embedded as is known in the art and then stained with Hematoxylin and Eosin in a standard fashion. These slides were examined and graded in a blinded fashion by a board certified pathologist.

RESULTS

Figure 1:
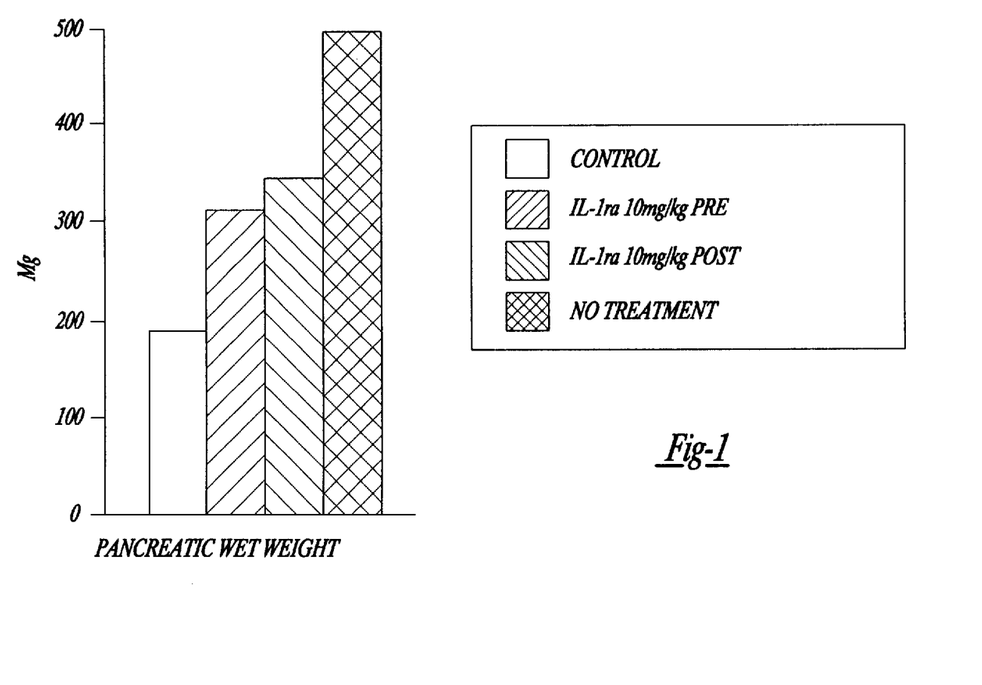
FIG. 1 is a graph showing the pancreatic wet weight in controls (shaded), IL-1ra 10 mg/kg pretreatment (solid), IL-1ra 10 mg/kg post-treatment (diagonal), and untreated disease control (cross-hatching) with * indicating $p<0.01$ compared to no treatment.
Figure 2:
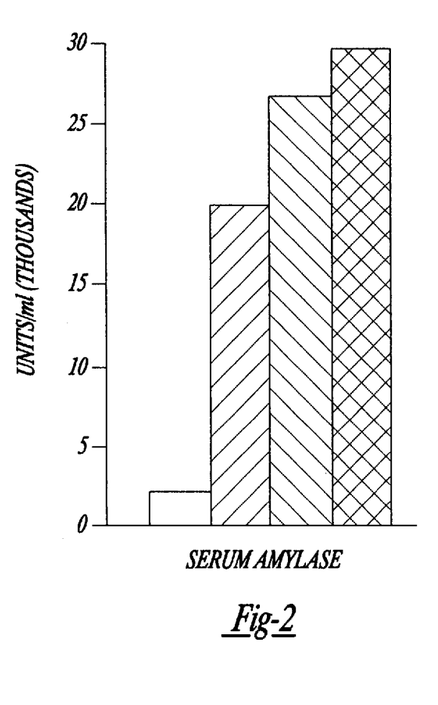
FIG. 2 is a graph showing the serum amylase levels in groups as in FIG. 1 with * indicating $p<0.05$ compared to no treatment.
Figure 3:
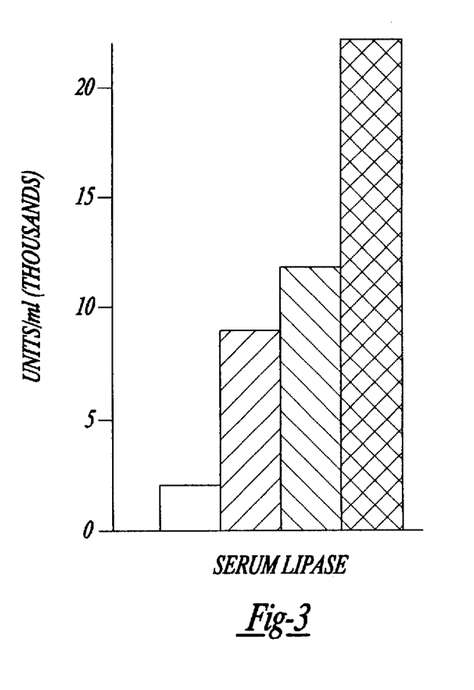
FIG. 3 is a graph showing the serum lipase levels in groups as in FIG. 1 with * indicating $p<0.0001$ compared to no treatment.
Figure 4:
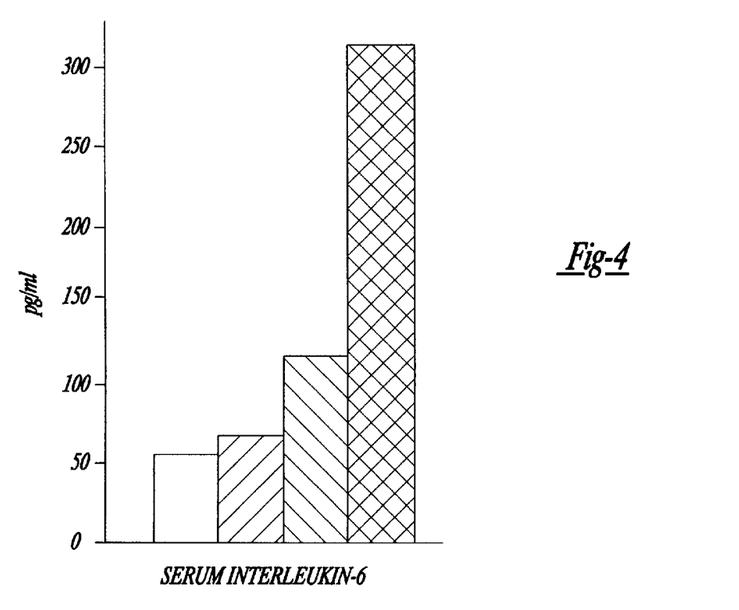
FIG. 4 is a graph showing the serum interleukin-6 levels in groups as in FIG. 1 with * indicating $p<0.0001$ compared to no treatment.
Figure 5:
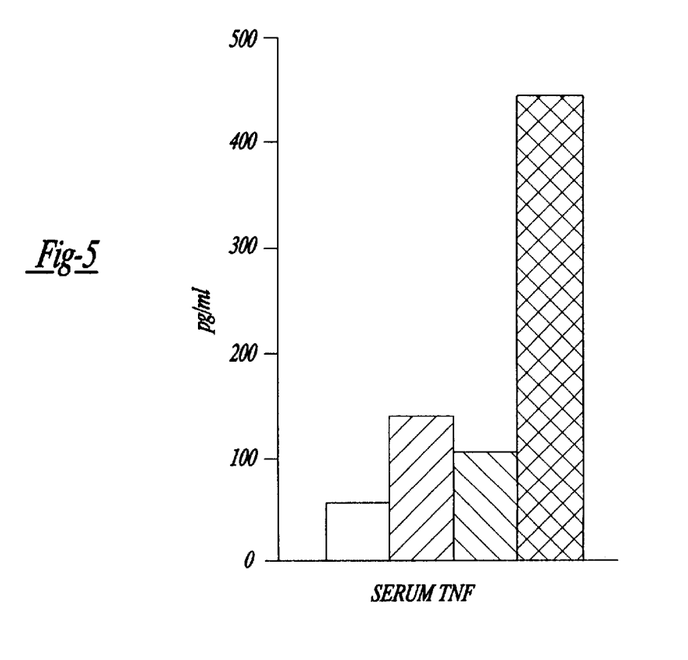
FIG. 5 is a graph showing the serum TFN levels in groups as in FIG. 1 with * indicating $p<0.0001$ compared to no treatment.

In these experiments, acute pancreatitis was induced in 45 mice using caerulein. Acute edematous, necrotizing pancreatitis is present within an hour of caerulein injection and reaches a peak effect approximately nine hours later. By treating mice with IL-1ra prior to or after the induction of pancreatitis, applicants were able to show a significant decrease in pancreatic wet weight ($p<0.01$), serum amylase ($p<0.05$), lipase ($p<0.0001$), and IL-6 ($p<0.0001$) as shown in FIGS. 1–4 and Table I, respectively. TNF ($p<0.0001$) was also significantly reduced (FIG. 5). All statistics noted are significant by two-tailed Wilcoxon test. Additionally, there was a decrease in the number of polymorphonuclear white blood cells (PMNs) within the capillaries of the lungs and pancreas. Histologic studies of these pancreata were performed in a blinded fashion and showed a significant decrease ($p<0.05$) in total organ edema, acinar necrosis, acinar vacuolization, and inflammation in those animals treated with IL-1ra. An important finding in these experiments was that treatment with IL-1ra within two hours after the onset of pancreatitis was nearly as protective as pretreatment.

These series of experiments were repeated using both higher and lower does of Il-1Ra. In one experiment, all animals received IL-1ra at a dose of 100 mg/kg/hrX3. All the previous findings were confirmed, but no significant benefit could be found with the higher dose. When the dose of IL-1ra was decreased to 1 mg/kg/hrx3, the benefits were seen in all categories except amylase levels. This dose, however, did not show quite as much decrease in wet weight or the levels of IL-6 and TNF as did the 10 mg/kg/hrx3 dose. These dose response experiments confirm the efficacy of IL-1ra in the treatment of pancreatitis when proper levels of the drug are maintained.

The cytokine activation in fulminant pancreatitis is similar to that of sepsis. The blockade of the cascade applicants have shown is similar to that shown in animal and human studies using IL-1ra for sepsis. A better understanding of the role played by specific cytokines in this systemic reaction has provided insight into effective therapies for severe pancreatitis, in particular the therapeutic use of IL-1ra in acute pancreatitis.

EXAMPLE 2

Experimental Methods:

The ICE antagonist VE-13045, a peptidyle ICE inhibiter (Vertex Pharmaceuticals, Inc., Cambridge, Mass.) was administered prior to the induction of acute edematous, necrotizing pancreatitis in adult male mice by injection of caerulein, a cholecystokinin antagonist (50 μg/kg IP q 1 hourx4) (Norman et al., 1995a, 1995b). The severity of pancreatitis was quantified by serum amylase, lipase, and blinded histologic grading.

Results.

As expected, administration of the ICE antagonist blocked the production of IL-1, and none of the animals receiving the drug showed an elevation of serum IL-1 ($p<0.001$ vs Control by 2 tailed Students t test). Administration of the ICE antagonist significantly decreased the expected rise in amylase and lipase ($p<0.01$). Pancreatic edema, necrosis, and inflammatory cell infiltrate were significantly diminished ($p<0.05$) by histologic grading in all animals receiving the antagonist.

Conclusions.

Blockade of the ICE enzyme eliminates the expected production of massive amounts of the inflammatory cytokine IL-1 during severe pancreatitis. This lack of tissue and circulating IL-1 results in the lessened severity of pancreatitis.

EXAMPLE 3

Experimental Methods:

Adult male transgenic C57/BL6 mice which were shown to be homozygous (-/-) for the gene encoding the ICE enzyme (Kuida et al., 1995) were utilized in a model of severe necrotizing pancreatitis, by injection of caerulein, a cholecystokinin antagonist (50 μg/kg IP q 1 hourx4). These animals have been shown to make no IL-1 in response to septic stimuli because the enzyme required for its production is not produced. Normal mice of the same strain were utilized as controls, with all animals receiving caerulein pancreatitis as outlined in Example 2 herein above. The severity of pancreatitis was assessed by serum amylase, lipase and blinded histologic grading as previously.

Results.

Figure 6:
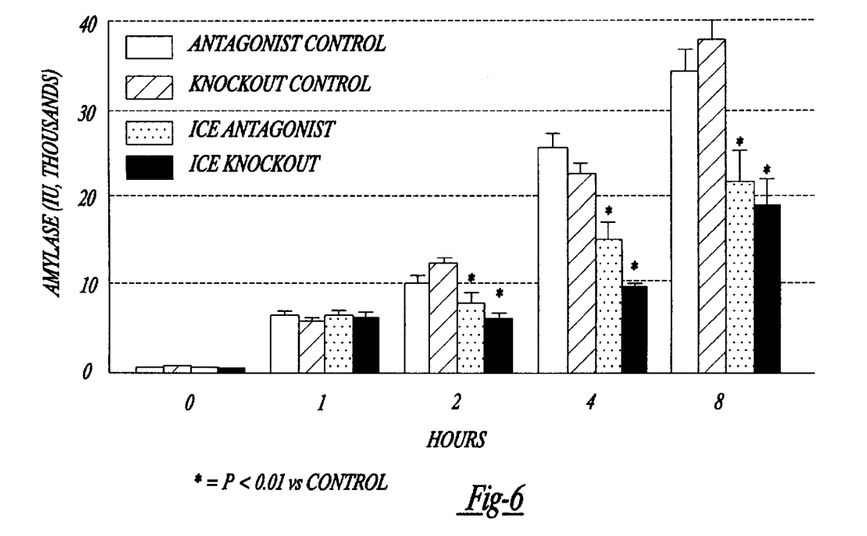
FIG. 6 is a bar graph showing the serum amylase levels in ICE knockout and control animals after pancreatitis disease induction, with Antagonist control (□), Knockout control (diagonal), ICE Antagonist (stippled), ICE Knockout (■) and * indicating $p<0.01$ compared to controls.
Figure 7:
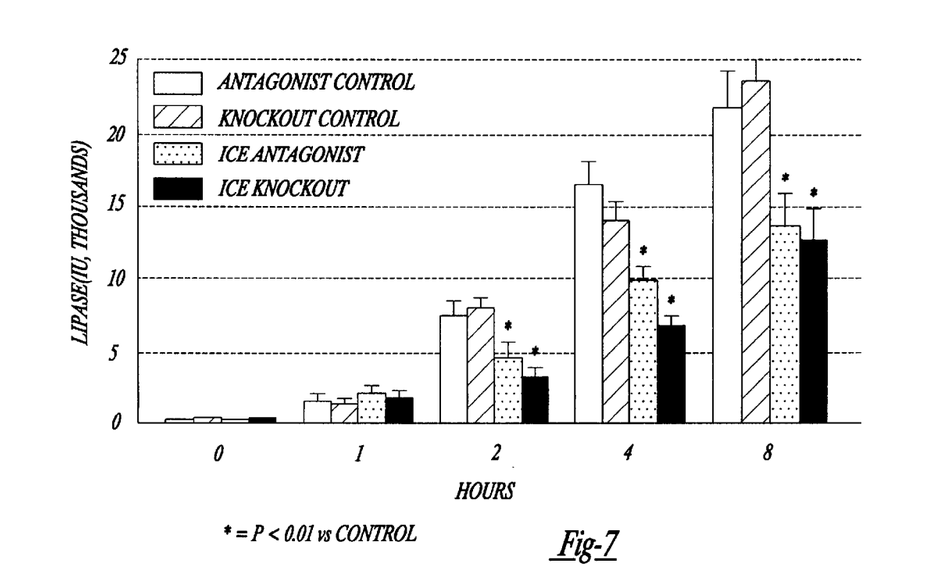
FIG. 7 is a bar graph showing the serum lipase levels in ICE knockout and control animals as in FIG. 6 after pancreatitis disease induction, with * indicating $p<0.01$ compared to controls.

The maximal amylase (FIG. 6) and lipase (FIG. 7) release from the ICE knockout animals was significantly less than the maximal release in the control animals (both $p<0.01$). Blind histologic grading showed significantly less edema, inflammation and overall histologic severity score (all $p<0.05$ vs Control).

Conclusions.

The genetic deletion of the ICE gene confirms antagonism studies showing that when the ICE enzyme is not active, no IL-1 is produced. When no IL-1 is circulating within tissues or within the serum, the destruction of the pancreatitis is less and the severity of pancreatitis is attenuated.

Throughout this application, various publications, including United States patents, are referenced by citation or number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE I

| GROUP | WET WT (mg) | AMYLASE (SU) | LIPASE (IU) | IL-6 (ng/kg) | TNF (ng/kg) |
|---|---|---|---|---|---|
| 1 | 188 ± 0.1 | 2204 ± 156 | 715 ± 58 | 54 ± 5 | 63 ± 9 |
| 2 | 493 ± .04* | 29465 ± 1756* | 22259 ± 3155* | 315 ± 51* | 442 ± 30* |
| 3A | 320 ± .02** | 21480 ± 2393** | 8976 ± 1685** | 65 ± 11** | 136 ± 3** |
| 4A | 341 ± .04** | 28088 ± 4494** | 11916 ± 2648** | 118 ± 17** | 101 ± 10** |

Results are expressed as mean ± SEM, significance accepted if $p < 0.05$ by two-tailed Wilcoxon test.
*compared to control (Group 1)
**compared to untreated pancreatitis (Group 2)

REFERENCES

Aiura K, Gelfand J A, Wakabayashi G, et al: Interleukin-1 receptor antagonist blocks hypotension in a rabbit model of gram-positive septic shock. Cytokine 4:498, 1991.

Bamba T, Yoshioka U, Inoue H, et al: Serum levels of interleukin-1 beta and interleukin-6 in patients with chronic pancreatitis. J. Gastroenterology 29 (3):314–19, 1994.

Bloedos D C, Stiles D M, Beshore A L, et al: Intravenous disposition of interleukin-1 receptor antagonist in healthy volunteers. Amer Soc Clin Pharmacology and Therapeutics March, 1992. Orlando, Fla. (Abstract)

Cioffi W C, Burleson D G, Pruit B A: Leukocyte responses to injury. Arch Surg 128:1235–41, 1993.

Coticchia J M, Lessler M J A, Carey L C, et al: Peritoneal fluid in human acute pancreatitis blocks hepatic mitochondrial respiration. Surgery 100 (5):850–855, 1986.

Deitch E A: Multiple organ failure. Ann Surg 216:117–134 1992.

Dinarello C A, Gelfand J A, Wolf S M: Anticytokine strategies in treatment of systemic inflammatory response syndrome. JAMA 269:1829–1834, 1993.

Dolan S, Campbell G, Rowlands B J: Biphasic tumor necrosis factor release in experimental acute pancreatitis. Gut 35:A575, 1994. (Abstract)

Driscoll, J. S, The Preclinical New Drug Research Program of the National Cancer Institute (1984) Cancer Treatment Reports 68:63–76.

Ellison E C, Pappas T N, Johnson J A, et al: Demonstration and characterization of the hemoconcentrating effect of ascitic fluid that accumulates during hemorrhagic pancreatitis. J Surg Research 30:241–248, 1981.

Fischer E, Marano M A, Van Zee K J, et al: Interleukin-1 receptor blockade improves survival and hemodynamic performance in *Escherichia coli* septic shock, but never fails to alter host responses to sublethal endotoxemia. J Clin Invest 89:1551, 1992.

Fischer E, Marano M A, Barber A, et al: A comparison between the effects of interleukin-1 administration and sublethal endotoxemia in primates. Am J Physiol 261:R442, 1991.

Formela L J, Mclaughlin P J, Flanagan B F, et al: Demonstration of tumor necrosis factor in pancreatic acinar cells by in situ hybridisation in a model of acute pancreatitis. Gut 35:A575, 1994 (Abstract)

Granowitz E V, Porat R, Mier J W, et al: Pharmacokinetics, safety and immunomodulatory effects of human recombinant interleukin-1 receptor antagonist in healthy humans. Cytokine 4:353, 1992.

Granowitz E V, Clark B D, Vannier E, et al: Effect of Interleukin-1 (IL-1) blockade on cytokine synthesis: I. IL-1 receptor antagonist inhibits IL-1-induced cytokine synthesis and blocks the binding of IL-1 to its type II receptor on human monocytes. Blood 79:2356–2363, 1992b.

Grewal H P, Mohey el Din A, Gaber L, et al: Amelioration of physiologic and biochemical changes of acute pancreatitis using an anti-TNF-α polyclonal anti body, Amer J Surg 167:214–19, 1994a.

Grewal H P, Kotb M, Mohey el Din A, et al: Induction of tumor necrosis factor in severe acute pancreatitis and its subsequent reduction after hepatic passage. Surgery 115 (2):213–221, 1994b.

Grewal H P, Hughes C B, Mohey el Din A, et al: Anti-TNF therapy improves survival and ameliorates the pathophysiologic sequelae in acute pancreatitis in the rat. Gastroenterology 106:163, 1994.

Gross V, Leser H-G, Heinisch A, et al: Inflammatory mediators and cytokines-new aspects of pathophysiology and assessment of severity of acute pancreatitis?. Hepato-Gastroenterol 40:522–529, 1993.

Guice K S, Oldham K T, Remick D G, et al: Anti-tumor necrosis factor antibody augments edema formation in caerulein-induced pancreatitis. J Surg Res 51:495–499. 1991.

Guice K S, Oldham K T, Caty M G, et al: Neutrophil-dependent, oxygen-radical mediated lung injury associated with acute pancreatitis. Ann Surg 210:740–747, 1989.

Heath, D I, Cruickshank A, Gudgeon M, et al: Role of interleukin-6 in mediating the acute phase protein response and potential as an early means of severity assessment in acute pancreatitis. Pancreas 66:41–45, 1993.

Imrie C W, Whyte A S: A prospective study of acute pancreatitis. Br J Surg 62:490–494, 1975.

Jacobs M L, Daggett W M, et al: Acute pancreatitis: Analysis of factors influencing survival. Ann Surg 185:43–51, 1977.

Kelly D M, McEntree G P, McGeeney K F et al: Microvasculature of the pancreas, liver, and kidney in caerulein-induced pancreatitis. Arch Sug 128:293–295, 1993.

Kuida K, Lippke J, Ku G, et al: Altered cytokine export and apoptosis in mice deficient in interleukin-1β converting enzyme. Science, 1995.

Kusske A M, Rongione A J, Ashley S W, et al. Interleukin 10 (IL-10) prevents death in lethal necrotizing pancreatitis (AP) in mice. Society of Uniersity Surgeons 57th Annual Meeting Feb., 1996, pg 40 (abstract).

Larsen G L, and Henson P M: Mediators of inflammation. Ann. Rev. Immunol 1:335–359, 1983.

Leach S D, Gorelick S, Modlin I M: New perspectives on acute pancreatitis. Scan J Gastroenterol 27 Suppl 192:29–38, 1992.

Lowry S F: Cytokine mediators of immunity and inflammation. Arch Surg 128:1235–1241, 1993.

Manso M A, San Roman J I, de Dios I, Garcia L J, and Lopez M A: Caerulein-induced acute pancreatitis in the rat. Digestive Disease and Sciences 37:364–368, 1992.

McKay C, Gallagher G, Baxter J N, et al: Systemic complications in acute pancreatitis are associated with increased monocyte cytokine release. Gut 35:A575, 1994 (Abstract).

Michie H R, Wilmore D W: Sepsis, signals, and surgical sequelae. Arch Surg 125:531–536, 1990.

Mohler, K M: The use of soluble TNF receptors as inhibitors of inflammation. Proceedings of regulation of cytokine activity for therapeutic development-Control of inflammation, growth and differentiation. Mar. 3, 1994, Washington, D.C. (Abstract).

Murayama K M, Drew J B, and Joehl R J: Does somatostatin analogue prevent experimental acute pancreatitis? Arch Surg 125:1570–1572, 1990.

Norman J, Franz M, Messina J, et al: Intrinsic production of pro-inflammatory cytokines by pancreas during acute pancreatitis. Surg Forum XLV:191–194, 1994a.

Norman J, Franz M: Acute phase cytokines during experimental acute pancreatitis. Cytokine, 1994b (in press)

Norman J, Franz M, Messina J, et al: Decreased severity of experimental acute pancreatitis by pre or post treatment with Interleukin-1 receptor antagonist. 28th Annual Meeting, Pancreas Club, Inc. (New Orleans, La.) May 1994c; p. 23. (Abstract)

Norman J, Franz M, Fink G, et al: Decreased mortality of experimental acute pancreatitis by pre or post treatment with Interleukin-1 receptor antagonist. 28th Annual Meeting, Pancreas Club, Inc. (New Orleans, La.) May 1994d Norman J, Franz M, Messina J, et al: Interleukin-1 receptor antagonist decreases severity of experimental acute pancreatitis. Surgery, 117:648–655, 1995a.

Norman J, Franz M, Fink G, et al: Decreased mortality of severe acute pancreatitis after proximal cytokine blockade. Annals of Surgery 221:625–634, 1995b.

Ohlsson K, Bjork P, Bergenfeldt M, et al: An interleukin-1 receptor antagonist reduces mortality from endotoxin shock. Nature 348:550, 1990.

Okusawa S, Gelfand J A, Ikejima T, et al: Interleukin-1 induces a shock-like state in rabbits. Synergism with tumor necrosis factor and the effect of cyclooxygenase inhibition. J Clin Invest 81:1162, 1988.

Oppenheim J J, Rossia J L, Gearing A J H: Clinical applications of cytokines; Role in pathogenesis diagnosis and therapy (Oxford University Press, New York, N.Y.) pp. 1–27, 1993.

Pappas T N, Lessler M A, Ellison E C, et al: Pancreatitis-associated ascitic fluid: Effect on oxygen consumption of liver cells. Soc Exp Biol Med 187:565–573, 1978.

Physicians' Desk Reference®: pp. 1654–1658, 1994.

Ranson J H C, Spencer F C: Role of peritoneal lavage in severe acute pancreatitis. Ann Surg 187:565–573, 1978.

Rodgers R E, Carey L V: Peritoneal lavage in experimental pancreatitis in dogs. Amer J Surg 111:792–794, 1966.

Saluja A, Saito I, Saluja M, Houlihan M J, Powers R E, Meldolesi J, and Steer ML: In vivo rat pancreatic acinar cell function during supramaximal stimulation with caerulein. Amer Physiological Society 1985: G702–G710.

Schoenberg M H, Büchler M, Beger H G: The role of oxygen radicals in experimental acute pancreatitis. Free Radical Biology & Medicine 12:515–522, 1992.

Spillenaar Bilgen E J, Marquet R L, Baumgartner D, et al: Attempts to reduce post-transplant pancreatitis in rats and dogs with the somatostatin analogue SMS 201–995. Transplant Proceed 21:2829–2830, 1989.

Steer M L: How and where does acute pancreatitis begin? Arch Surg 127:1350–1353, 1992.

Steinberg W, Tenner S: Acute pancreatitis. N Eng J Med 330:1198–1220, 1994.

Stone H H, Fabian T C: Peritoneal dialysis in treatment of acute alcoholic pancreatitis. Surg Gynecol Obstet 150:878–882, 1980.

Tani S, Otsuki M, Itoh H, et al: Histologic and biochemical alterations in experimental acute pancreatitis induced by supramaximal caerulein stimulation. Intl J Pancreatology 2:337–348, 1987.

Van Ooijen B, Kort W J, Tinga C J, et al: Significance of thromboxane $A_2$ and Prostaglandin $I_2$ in acute necrotizing pancreatitis in rats. Digestive Disease and Sciences 35:1078–1084, 1990.

Waage A, Espevik T: Interleukin-1 potentiates the lethal effect of tumor necrosis factor/cachectic in mice. J Exp Med 167:1987, 1988.

Wakabayashi G, Gelfand J A, Burke J F, et al: A specific receptor antagonist for interleukin-1 prevents *E. coli* induced shock in rabbits. FASEB 5:338, 1991.

Zhu Z H, Holt S, El-Lbishi M S, et al: A somatostatin analogue is protective against retrograde bile salt-induced pancreatitis in the rat. Pancreas 6:609–613, 1991.

What is claimed is:

1. A method for treating pancreatitis which comprises administering to a patient afflicted with pancreatitis an effective amount of a peptidyl Interleukin-1 converting enzyme (ICE) inhibitor carbobenzyloxy-Val-Ala-Asp(O-Et)-$CH_2$O-dichlorobenzoate or a pharmaceutically acceptable salt thereof in combination with an effective amount of Interleukin-1 receptor antagonist (IL-1ra) or a pharmaceutically acceptable salt thereof wherein the effective amount of the peptidyl ICE inhibitor and IL-1ra administered is from 100 ng/kg body weight to 100 mg/kg body weight of the patient per day.

2. The method as set forth in claim 1 wherein pancreatitis is an acute pancreatitis.

3. The method as set forth in claim 1 wherein pancreatitis is a chronic pancreatitis.

4. The method of claim 1 wherein the peptidyl ICE inhibitor and IL-1ra are suspended in an acceptable carrier.

5. The method of claim 1 wherein the effective amount of the peptidyl ICE inhibitor is administered initially by an intravenous injection to bring blood levels to a suitable level after which the patient's peptidyl ICE inhibitor levels are maintained for as long as clinically indicated.

6. The method of claim 1 further comprising administering cytokine cascade blockers in combination with the peptidyl ICE inhibitor, wherein the cytokine cascade blocker is selected from the group consisting of interleukin-1 receptor antagonist (IL-1ra) and tumor necrosis factor soluble receptor (TNFsr).

* * * * *